United States Patent [19]

Conway

[11] 3,976,774
[45] Aug. 24, 1976

[54] ANTIEMETIC METHOD
[75] Inventor: Alvin C. Conway, North St. Paul, Minn.
[73] Assignee: Riker Laboratories, Inc., Northridge, Calif.
[22] Filed: June 2, 1975
[21] Appl. No.: 583,041

[52] U.S. Cl. ............................................. 424/250
[51] Int. Cl.² ...................................... A61K 31/495
[58] Field of Search ................... 424/250; 260/268

[56] References Cited
UNITED STATES PATENTS 3,860,652  1/1975  Hammar ........................ 260/570.9
3,904,630  9/1975  Hammer et al. ............... 260/268 PC Primary Examiner—Leonard Schenkman
Attorney, Agent, or Firm—Alexander, Sell, Steldt & DeLaHunt

[57] ABSTRACT

A method of preventing emesis in mammals is disclosed which comprises administering to mammals in need thereof the compound anti-8-methylpiperazinyl-N'-carbonyldibenzobicyclo[3.2.1]octadiene or a pharmaceutically acceptable acid addition salt thereof.

5 Claims, No Drawings

ANTIEMETIC METHOD

BACKGROUND OF THE INVENTION

This invention relates to a method of preventing emesis in mammals. More specifically, this invention relates to the use of the known compound anti-8-N-methyl-piperazinyl-N'-carbonyldibenzobicyclo[3.2.1]octadiene and its pharmaceutically acceptable acid addition salts as antiemetic agents.

Antiemetic agents are useful in alleviating nausea and vomiting associated with common conditions such as motion sickness. These agents are also useful in preventing emesis induced in patients receiving radiation therapy or in patients undergoing various drug therapies in which emesis is a common side effect. Examples of drugs which frequently produce emesis are apomorphine used to treat Parkinsonism, cardiac glycosides used in the treatment of congestive heart failure and protoveratrine used to lower blood pressure. Concurrent administration of an antiemetic agent with these drugs often increases the dose of the drug which a patient can tolerate and allows therapeutic drug levels to be achieved.

DESCRIPTION OF THE PRIOR ART

Compounds wherein the dibenzobicyclo[3.2.1]octadiene nucleus is bonded at the 8 position through a carbonyl or an alkylene group to an amino group are known. U.S. Pat. No. 3,860,652 describes compounds wherein an amino residue ($-NR_2$) is linked to a dibenzobicyclo[3.2.1]octadiene nucleus at the 8 position through an alkylene or alkenylene group. These compounds are disclosed as having antidepressant and anticonvulsant activity.

German Offenlegungsschrift No. 1,953,334 and No. 2,216,884 describe numerous 5,10-methano-5H-dibenzo[a,d]cycloheptenes. The nucleus of these compounds is the same as the dibenzobicyclo[3.2.1]octadiene nucleus of the compounds of the present invention, an alternative naming and numbering system being employed. The 12-position of the compounds described in these German references corresponds to the 8-position of the compounds described herein.

German Offenlegungsschrift No. 1,953,334 discloses compounds having a hydroxy substituent in the 5-position and additionally, several derivatives of the nucleus including 12-carboxyamido-5,10-methano-5H-dibenzo[a,d]cycloheptene. These compounds are described as diuretic agents.

German Offenlegungsschrift No. 2,216,884 discloses antidepressant and anticonvulsant compounds in which an amino residue is linked to the 5,10-methano-5H-dibenzo[a,d]-cycloheptene nucleus at the 12-position. The 12-N-methyl piperazinyl derivative, corresponding to the free base compound of the present invention, is disclosed therein as an intermediate.

The compound anti-8-N-methylpiperazinyl-N'-carbonyldibenzobicyclo[3.2.1]octadiene used in the method of the present invention is disclosed in U.S. Pat. No. 3,904,630. This disclosure describes the compound and its pharmaceutically acceptable acid addition salts as having utility as sedatives and tranquilizing agents. So far as is known, the prior art has not disclosed or suggested the use of these compounds or other compounds containing the dibenzobicyclo[3.2.1]-octadiene nucleus as antiemetic agents.

DESCRIPTION OF THE INVENTION

The present invention relates to a method for preventing emesis in mammals which comprises administering to said mammals at least an effective amount of a compound selected from the group consisting of 8-anti-N-methylpiperazinyl-N'-carbonyldibenzobicyclo[3.2.1]octadiene and pharmaceutically acceptable acid addition salts thereof.

The free base form of the compound used in this method has the following structure and number system:

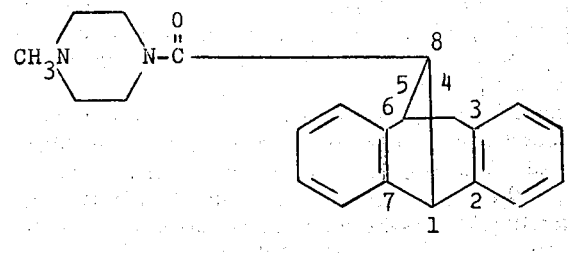

This compound is prepared by the reaction of N-methylpiperazine with an acyl halide derivative, preferably the chloride of 8-anti-carboxydibenzobicyclo[3.2.1]octadiene, in an inert solvent such as dichloromethane, chloroform, benzene, hexane, and the like.

The necessary intermediate, 8-anti-carboxydibenzobicyclo[3.2.1]octadiene, is prepared from the known compound 8-anti-chlorodibenzocyclo[3.2.1]octadiene, see J. Am. Chem. Soc. 87, 2877 (1965).

The reaction proceeds rapidly to completion in less than one hour at a temperature of 20 to 30°C. The product is readily isolated by removal of the solvent, and is purified by recrystallization or other conventional method.

The free base product is readily converted to an acid addition salt by treatment with an approximately equimolar quantity of an acid. This is conveniently and readily accomplished by treating the free base in isopropyl alcohol solution with the selected acid in equimolar amounts to precipitate the product salt. Optionally, the precipitation may be facilitated by the addition of a nonsolvent for the salt. The compounds generally have been found to incorporate some water of crystallization.

It is well known that pharmaceutically acceptable acid addition salts can be prepared from the corresponding pharmacologically active base. These salts are essentially equivalent to the base with respect to therapeutic activity and toxicity. In some cases, the acid addition salts may offer advantages in formulation and absorption due to their increased water solubility.

Pharmaceutically acceptable acid addition salts useful in the method of the invention may be organic or inorganic, and include the hydrochloride, hydrobromide, maleate, sulfate, phosphate, acetate, lactate, tartrate, citrate, organic sulfonates such as methanesulfonates, and the like.

The activity of the compounds used according to the invention was determined in standard pharmacological screening tests for detection of antiemetic activity in mammals. The test method employed is similar to that described by Staniszewski in Arch. int pharmacodyn., 1960 CXXIV, No. 1-2, pp. 263-273, and assays the ability of a test compound to antagonize apomorphine-induced emesis in the dog.

Compounds of the invention were also found to protect against emesis induced by protoveratrine B (veratetrine).

The method of the present invention may be practiced by administering the compounds subcutaneously, intraperitoneally or orally. When administered subcutaneously, the compound is administered in solution in a pharmaceutically acceptable solvent. Subcutaneous doses will generally range from about 0.5 to 20 milligrams per kilogram of body weight of the subject. It is presently preferred to administer the compounds orally in doses of from 1 to 40 milligrams per kilogram. Such doses provide good therapeutic ratios as the oral $LD_{50}$ dose of the compounds has been found to be quite high, i.e., approximately 1525 mg/kg in the rat for the hydrochloride salt.

The dose administered must be varied according to the conditions and response of the individual subject treated. Factors such as age, weight, general health, etc. of the subject will influence the dosage. It is well within the skill of the medical practitioner to determine the proper dosage for each subject.

The compounds of the invention may be administered in any conventional drug dosage form. The salts are water-soluble and can be readily formulated into solutions with known pharmaceutically acceptable solvents. For oral dosage, the compounds may be conveniently administered as pills or capsules, generally in admixture with conventional diluents and excipients.

The following nonlimiting examples are provided to illustrate the best mode presently known for the preparation and use of the compounds of this invention.

EXAMPLE 1

To a suspension of 3.15 g. (0.130 mole) of magnesium filings in 20 ml. of tetrahydrofuran at reflux temperatures were added 29.5 g (0.126 mole) of 8-anti-chlorodibenzobicyclo[3.2.1]-octadiene. While maintaining the solution at reflux, five drops of 1,2-dibromomethane were added and reflux was continued for about 16 hours. The mixture was cooled to −25°C with a dry ice-acetone bath, and carbon dioxide was bubbled in rapidly. The addition of carbon dioxide was continued for 1.5 hours after which the mixture was warmed to room temperature. The mixture was added carefully to an aqueous solution unsaturated with ammonium chloride. The water layer was separated and extracted with dichloromethane, followed by extraction with diethyl ether. The organic layers obtained from the extractions were combined. The combined organic layers were evaporated under reduced pressure to a non-volatile residue. Diethyl ether was added and the ether solution was washed twice with equal volumes of 5 percent aqueous sodium hydroxide solution. The aqueous solution was acidified and washed with dichloromethane. The dichloromethane extracts were combined and dried over magnesium sulfate. This solution was filtered, and the filtrate evaporated under reduced pressure to provide 8-carboxydibenzobicyclo[3.2.1]-octadiene. This solid product was fractionally recrystallized from benzene to provide a white solid, melting point 175°–180°C. Nuclear magnetic resonance analysis of this product showed it to be essentially the pure (greater than 95 percent) anti-isomer.

Analysis: Calculated for $C_{17}H_{14}O_2$: %C, 81.5; %H, 5.64;

Found: %C, 81.8; %H, 5.60.

EXAMPLE 2

A solution of 50 ml. of thionyl chloride and 7.8 g (0.032 mole) of anti-8-carboxydibenzobicyclo[3.2.1]octadiene was heated to its reflux temperature and maintained at reflux temperature for one hour. The excess thionyl chloride was removed by evaporation under reduced pressure. Benzene (about 50 ml.) was then added, and the mixture was again evaporated to dryness under reduced pressure. The solid product was anti-8-carboxy-dibenzobicyclo[3.2.1]octadiene chloride, m.p. 102°–104°C.

EXAMPLE 3

The anti-8-carboxydibenzobicylooctadiene chloride product (0.032 mole) from Example 2 was dissolved in dichloromethane and 10 g (0.100 mole) of N-methylpiperazine was added with stirring. After 30 minutes, the mixture was washed successively with equal volumes of water, saturated sodium bicarbonate solution and saturated sodium chloride solution. The organic layer was then dried over anhydrous sodium sulfate and filtered. The filtrate was evaporated under vacuum giving an oil which solidified when washed with hexane. The solid product was triturated with hexane and filtered, yielding the solid free base, 8anti-(N-methylpiperazino-N'-carbonyl)dibenzobicyclo[3.2.1]octadiene, m.p. 172°–174°C. (uncorrected). The structure of the product was verified by infrared spectral analysis.

EXAMPLE 4

To a suspension of 8.5 g (0.039 mole) of 8-anti-(N-methylpiperazino-N'-carbonyl)dibenzobicyclo[3.2.1]octadiene base in 100 ml. of isopropanol were added 7 ml. of 7M hydrogen chloride in isopropanol to form the hydrochloride salt of the base. The solution was treated with diisopropyl ether to cause precipitation of the salt which was separated by filtration. The solid was recrystallized from a mixture of isopropyl alcohol and diisopropyl ether. A tank solid, 8-anti-(N-methylpiperazino-N'-carbonyl)-dibenzobicyclo[3.2.1]octadiene hydrochloride was obtained, m.p. 265°–267°C.

Analysis:

Calculated for $C_{22}H_{24}N_2O \cdot HCl \cdot 1/2H_2O$: %C, 69.4; %H, 6.8; %N 7.4;

Found: %C, 69.9; %H, 6.9; %N, 7.4.

EXAMPLE 5

A total of eight non-fasted dogs were used with one week rest between trials. The dogs were injected subcutaneously with a dose of 20 (1 dog), 10 (1 dog), 5 (1 dog), 2 (6 dogs) and 1 (6 dogs) mg/kg of anti-8-N-methylpiperazinyl-N'-carbonyl-dibenzobicyclo[3.2.1]octadiene hydrochloride in water solution. About equal numbers of dogs were used as controls and injected subcutaneously with saline solution. Thirty minutes after treatment, each of the dogs was injected intravenously with 25 mcg/kg of aqueous apomorphine hydrochloride solution. The results are shown in the following table:

| Dose (mg/kg) | Number of Dogs | Dogs with Emesis | Dogs Protected | Number of emetic episodes |
|---|---|---|---|---|
| 0 (saline) | 14 | 14 | 0 | 3, 6, 3, 4, 5, 4, 6, 3, 3, 4, 3, 2, 3, 3, ($\bar{m}$ = 3.7) |
| 20 | 1 | 0 | 1 | — |
| 10 | 1 | 0 | 1 | — |
| 5 | 1 | 0 | 1 | — |
| 2 | 6 | 0 | 6 | — |
| 1 | 6 | 1 | 5 | 3 |

EXAMPLE 6

A total of six non-fasted dogs were used with a one week rest between trials. The dogs were administered oral doses of powdered anti-8-N-methylpiperazinyl-N'-carbonyl-dibenzobicyclo[3.2.1]octadiene hydrochloride in a gelatin capsule. The same six dogs were used as controls on one occasion and administered an oral dose of dextrose in a gelatin capsule. One hour after treatment, each dog was injected intravenously with 25 mcg/kg of aqueous apomorphine hydrochloride solution. The results are shown in the following table:

| Dose (mg/kg) | Number of Dogs | Dogs with emesis | Dogs Protected | Number of emetic episodes |
|---|---|---|---|---|
| 16 | 1 | 0 | 1 | — |
| 8 | 1 | 0 | 1 | — |
| 4 | 2 | 0 | 2 | — |
| 2 | 5 | 0 | 5 | — |
| 1 | 6 | 3 | 3 | 2, 5, 1 ($\bar{m} = 2.7$) |
| 0 | 6 | 6 | 0 | 5, 11, 2, 6, 4, 4 ($\bar{m} = 5.3$) |

EXAMPLE 7

A total of six non-fasted dogs were used with one week rest between trials. The dogs were administered subcutaneous doses of an aqueous solution of anti-8-N-methylpiperazinyl-N'-carbonyldibenzobicyclo[3.2.1]octadiene hydrochloride. About equal numbers of dogs were used as controls and administered a subcutaneous dose of saline. After varying time periods, the dogs were injected intravenously with 25 mcg/kg of aqueous apomorphine hydrochloride solution. The results are shown in the following table:

| Dose (mg/kg) | Post-treatment interval (hours) | Number of Dogs | Dogs with emesis | Dogs Protected | Number of emetic episodes |
|---|---|---|---|---|---|
| 0 (Saline control) | 0.5 or 1 | 15 | 15 | 0 | 3, 6, 3, 4, 5, 4, 6, 3, 3, 4, 3, 2, 3, 3, 2 ($\bar{m} = 3.6$) |
| 1 | 2.0 | 5 | 2 | 3 | 1,1 ($\bar{m} = 1.0$) |
| 2 | 2.0 | 6 | 0 | 6 | — |
| 2 | 4.0 | 6 | 3 | 3 | 2,2,2, ($\bar{m} = 2.0$) |
| 2 | 8.0 | 6 | 6 | 0 | 3, 4, 4, 3, 2, 3, ($\bar{m} = 3.2$) |
| 8 | 16.0 | 3 | 3 | 0 | 1, 3, 1, ($\bar{m} = 1.7$) |
| 12 | 16.0 | 3 | 1 | 2 | 1 |

Depressant and sedative behavioral effects were not present at doses of 1 and 2 mg/kg. (No observation of behavioral effects was made for the 16 hour post-treatment periods).

EXAMPLE 8

A total of six non-fasted dogs were used with one week rest between trials. The dogs were administered orally a gelatin capsule containing powdered anti-8-N-methylpiperazinyl-N'-carbonyl-dibenzobicyclo[3.2.1]octadiene hydrochloride.

Control non-fasted dogs received a gelatin capsule containing dextrose. After varying time periods, dogs were injected intravenously with 25 mcg/kg of aqueous apomorphine hydrochloride solution. The results are shown in the following table.

Nearly complete protection is noted 4 hours after treatment, while at 8 hours only residual protection was noted.

| Dose (mg/kg) | Post-treatment interval (hours) | Number of Dogs | Dogs with emesis | Dogs Protected | Number of emetic episodes |
|---|---|---|---|---|---|
| 0 | 4 | 6 | 6 | 0 | 5, 11, 2, 6, 4, 4 ($\bar{m} = 5.3$) |
| 2 | 4 | 6 | 1 | 5 | 8 |
| 2 | 8 | 6 | 5 | 1 | 2, 5, 1, 3, 3 ($\bar{m} = 2.8$) |

What is claimed is:

1. A method of preventing emesis in mammals which comprises administering to mammals in need thereof an effective amount of a compound selected from the group consisting of anti-8-N-methylpiperazinyl-N'-carbonyldibenzobicyclo[3.2.1]-octadiene and a pharmaceutically acceptable acid addition salt thereof.

2. The method of claim 1 wherein the compound is administered orally.

3. The method of claim 1 wherein the compound is administered subcutaneously.

4. The method of claim 1 wherein the compound is administered in an amount between 0.5 and 40 mg per kg of body weight.

5. The method of claim 1 wherein the compound is anti-8-methylpiperazinyl-N'-carbonyldibenzobicyclo[3.2.1]-octadiene hydrochloride.

* * * * *